US012173315B2

(12) United States Patent
Lee et al.

(10) Patent No.: US 12,173,315 B2
(45) Date of Patent: Dec. 24, 2024

(54) GROWTH AND SURVIVAL COMPOSITIONS FOR CELLS CAPABLE OF PRODUCING ANTIBODIES AND METHODS RELATED THERETO

(71) Applicant: Emory University, Atlanta, GA (US)

(72) Inventors: Frances Eun-Hyung Lee, Atlanta, GA (US); Ignacio Sanz, Atlanta, GA (US); Doan Nguyen, Atlanta, GA (US)

(73) Assignee: Emory University, Atlanta, GA (US)

( * ) Notice: Subject to any disclaimer, the term of this patent is extended or adjusted under 35 U.S.C. 154(b) by 645 days.

(21) Appl. No.: 17/406,212

(22) Filed: Aug. 19, 2021

(65) Prior Publication Data

US 2021/0380941 A1    Dec. 9, 2021

Related U.S. Application Data

(62) Division of application No. 15/735,933, filed as application No. PCT/US2016/036650 on Jun. 9, 2016, now Pat. No. 11,124,766.

(60) Provisional application No. 62/174,592, filed on Jun. 12, 2015, provisional application No. 62/328,439, filed on Apr. 27, 2016.

(51) Int. Cl.
*C12N 5/0781* (2010.01)
*A61K 35/00* (2006.01)

(52) U.S. Cl.
CPC ............ *C12N 5/0635* (2013.01); *A61K 35/00* (2013.01); *C12N 2500/02* (2013.01); *C12N 2500/32* (2013.01); *C12N 2500/34* (2013.01); *C12N 2500/38* (2013.01); *C12N 2500/60* (2013.01); *C12N 2501/2305* (2013.01); *C12N 2501/2306* (2013.01); *C12N 2501/2321* (2013.01); *C12N 2501/24* (2013.01); *C12N 2501/25* (2013.01); *C12N 2501/998* (2013.01); *C12N 2502/1358* (2013.01); *C12N 2533/52* (2013.01)

(58) Field of Classification Search
None
See application file for complete search history.

(56) References Cited

U.S. PATENT DOCUMENTS

| | | | |
|---|---|---|---|
| 4,259,447 | A | 3/1981 | Hafeli |
| 4,920,051 | A | 4/1990 | Edmunds |
| 11,124,766 | B2 | 9/2021 | Lee |
| 2002/0072089 | A1 | 6/2002 | Holtzman |
| 2005/0272152 | A1 | 12/2005 | Xu |
| 2011/0076253 | A1 | 3/2011 | Snyder |
| 2013/0295672 | A1 | 11/2013 | Planelles |
| 2014/0205563 | A1 | 7/2014 | Maguire |

FOREIGN PATENT DOCUMENTS

| | | |
|---|---|---|
| EP | 2540820 A1 | 2/2013 |
| EP | 2574666 A1 | 3/2013 |
| WO | 1998010056 | 3/1998 |
| WO | 2001055350 | 8/2001 |
| WO | 2006005153 | 1/2006 |
| WO | 2006015373 | 2/2006 |
| WO | 2006088972 | 8/2006 |
| WO | 2014132032 | 9/2014 |

OTHER PUBLICATIONS

Arora, Cell Culture Media: A Review, Mater Methods 2013, 3:175, available at https://www.labome.com/method/Cell-Culture-Media-A-Review.html.
Avery et al. BAFF selectively enhances the survival of plasmablasts generated from human memory B cells, J. Clin. Invest. 112:286-297 (2003).
Cassese et al. Plasma Cell Survival Is Mediated by Synergistic Effects of Cytokines and Adhesion-Dependent Signals, The Journal of Immunology, 2003, 171: 1684-1690.
Belnoue et al. APRIL is critical for plasmablast survival in the bone marrow and poorly expressed by early-life bone marrow stromal cells, Blood (2008) 111 (5): 2755-2764.
Benson et al. Cutting Edge: The Dependence of Plasma Cells and Independence of Memory B Cells on BAFF and APRIL, The Journal of Immunology, 2008, 180: 3655-3659.
Cocco et al. In Vitro Generation of Long-lived Human Plasma Cells, The Journal of Immunology, 2012, 189: 5773-5785.
Danet et al. Expansion of human SCID-repopulating cells under hypoxic conditions, J. Clin. Invest. 112:126-135 (2003).
Dilillo et al. Maintenance of Long-Lived Plasma Cells and Serological Memory Despite Mature and Memory B Cell Depletion during CD20 Immunotherapy in Mice, The Journal of Immunology, 2008, 180: 361-371.
Extended European Search Report, to EP App. No. 1120 / 3307070 PCT/U.S. Pat. No. 2016036650 dated Nov. 30, 2018.
Garimalla et al. Differential transcriptome and development of human peripheral plasma cell subsets, JCI Insight. 2019, 4(9):e126732.
Gomez et al. Basophils Support the Survival of Plasma Cells in Mice, The Journal of Immunology, 2010, 185: 7180-7185.
Halliley et al. Long-Lived Plasma Cells Are Contained within the CD19-CD38hiCD138+ Subset in Human Bone Marrow, 2015, Immunity 43, 132-145.
Jourdan et al. IL-6 supports the generation of human long-lived plasma cells in combination with either APRIL or stromal cell-soluble factors, Leukemia (2014) 28, 1647-1656.
Lanzavecchia, Long-term culture of normal and malignant plasma cells, available at http://www.irb.usi.ch/long-term-culture-normal-and-malignant-plasma-cells, printed 2016.

(Continued)

Primary Examiner — Michail A Belyavskyi
(74) Attorney, Agent, or Firm — Emory Patent Group

(57) ABSTRACT

This disclosure relates to growth media and environments for in vitro culturing of cells that produce or are capable of producing antibodies. In certain embodiments, the media comprises IL-6, fibronectin, and typically a saccharide. In certain embodiments, the disclosure contemplates cell culture compositions comprising IL-6 and fibronectin that are derived from proteins secreted from mesenchymal stromal/stem cells (MSCs). In certain embodiments, the disclosure contemplates enclosures comprising culture compositions disclosed herein that are in ambient air or optionally in an environment wherein oxygen is absent or at a low concentration.

7 Claims, 6 Drawing Sheets

Figure 1A:
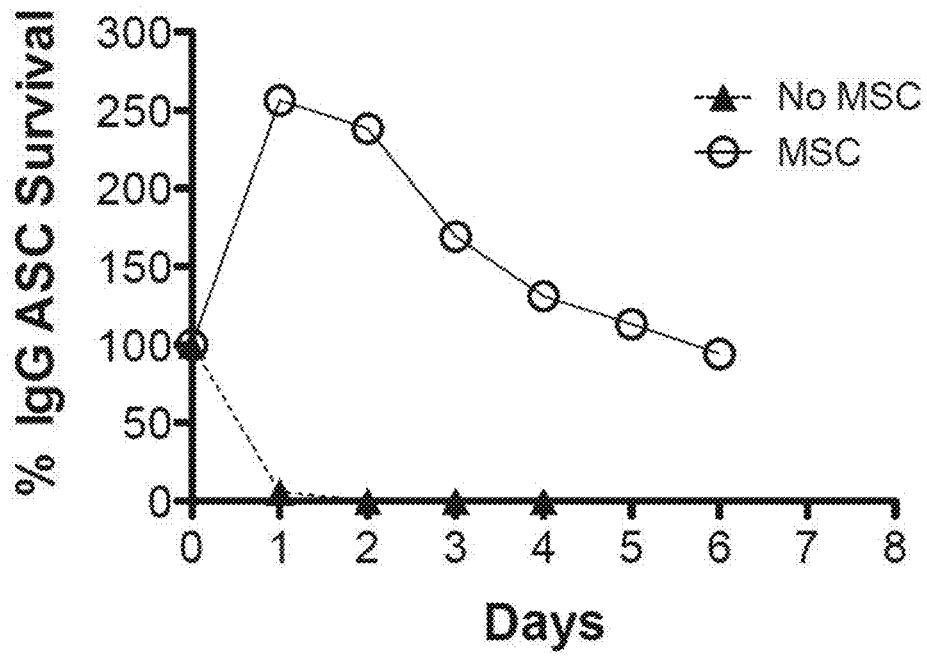

Specification includes a Sequence Listing.

(56) References Cited

OTHER PUBLICATIONS

Manz et al. Lifetime of plasma cells in the bone marrow, Nature, 1997, 388(6638):133-4.
Matsuda et al. A proliferation-inducing ligand sustains the proliferation of human naïve (CD27negative) B cells and mediates their differentiation into long-lived plasma cells in vitro via transmembrane activator and calcium modulator and cyclophilin ligand interactor and B-cell mature antigen, Cellular Immunology 295 (2015) 127-136.
McCarron et al. CD138 mediates selection of mature plasma cells by regulating their survival, Blood. 2017;129 (20):2749-2759.
Mesin et al. Long-Lived Plasma Cells from Human Small Intestine Biopsies Secrete Immunoglobulins for Many Weeks In Vitro, The Journal of Immunology, 2011, 187: 2867-2874.
Nguyen et al. Factors of the bone marrow microniche that support human plasma cell survival and immunoglobulin secretion, Nat Commun. 2018, 9(1):3698.
Nguyen et al. Extracellular vesicles from bone marrow-derived mesenchymal stromal cells support ex vivo survival of human antibody secreting cells, Journal of Extracellular Vesicles, 2018 vol. 7, 1463778, 14 pages.
OConnor et al. BCMA Is Essential for the Survival of Long-lived Bone Marrow Plasma Cells, J Exp Med. 2004; 199(1): 91-98.
Palumbo et al. Multiple Myeloma, N Engl J Med, 2011;364:1046-60.
Radbruch et al. Competence and competition: the challenge of becoming a long-lived plasma cell, Nat Rev Immunol. 2006, 6(10):741-50.
Roldan et al. VLA-4-Fibronectin Interaction Is Required for the Terminal Differentiation of Human Bone Marrow Cells Capable of Spontaneous and High Rate Immunoglobulln Secretion, J Exp Med. 1992, 175(6): 1739-1747.
Shapiro et al. Blimp-1 is required for maintenance of long-lived plasma cells in the bone marrow, J Exp Med. 2005, 202(11): 1471-1476.
Spencer et al. Direct measurement of local oxygen concentration in the bone marrow of live animals, Nature. 2014, 508(7495): 269-273.
Wols et al. The Role of Bone Marrow-Derived Stromal Cells in the Maintenance of Plasma Cell Longevity, The Journal of Immunology, 2002, 169: 4213- 4221.
Wols et al. The effects of microenvironment and internal programming on plasma cell survival, International Immunology, 2007, vol. 19, No. 7, pp. 837-846.

```
NP 003799.1       1   MPASSPFLLAPKGPPGNMGGPVREPALSVALWLSWGAALGAVACAMALLT  50
NP 001192059.1    1   MPASSPFLLAPKGPPGNMGGPVREPALSVALWLSWGAALGAVACAMALLT  50
NP 001192098.1    1   MPASSPSLLAPKGPPGDMGGPVREPALSVALWLSWGAALGAVACAMALLT  50
NP 001029819.1    1   MPASSPSLLSPKGPQGDMGGPVREPALSVALWLSWGAALGAVACAMVLLT  50
NP 076006.2       1   MPASSP---------GHMGGSVREPALSVALWLSWGAVLGAVTCAVALLI  41
NP 001009623.1    1   MPASSP---------GNMGGSVREPALSVTLWLSWGAVLGAVTCAVALLI  41

NP 003799.1       51  QQTELQSLRREVSRLQGTGGPSQNGEGYPWQSLPEQSSDALEAWENGERS  100
NP 001192059.1    51  QQTELQSLRREVSRLQRTGGPSQNGEGYPWQSLPEQSSDALEAWENGERS  100
NP 001192098.1    51  QQTELQNLRREVARLQRTGGPSEKEEGYPWLSLQEQSPDALEAWENGERS  100
NP 001029819.1    51  QQTELQTLRREVTRLQRNGGPSEKGEGNPWLNLQEQSPDGTEGQENGERS  100
NP 076006.2       42  QQTELQSLRREVSRLQRSGGPSQKQGERPWQSLWEQSPDVLEAWKDGAKS  91
NP 001009623.1    42  QQAELQSLRREVSRLQRSGGASQKRGEPPWQSLWEQSPDVLGAWKDGAKS  91

NP 003799.1       101 RKRRAVLTQKQKKQHSVLHLVPINATSKDDSDVTEVMWQPALRRGRGLQA  150
NP 001192059.1    101 RKRRAVLTQKQKKQHSVLHLVPINATSKDDSDVTEVMWQPALRRGRGLQA  150
NP 001192098.1    101 RRKRAALIHKQKKKHSVLHLVPINITSKEDSDVTEVMWQPALKRGRGLEA  150
NP 001029819.1    101 RRRRAVLTRKHKKKRSVLHLVPINITSKEDSDVTEVMWQPALQRGRGLEA  150
NP 076006.2       92  RRRRAVLTQKHKKKHSVLHLVPVNITSKADSDVTEVMWQPVLRRGRGLEA  141
NP 001009623.1    92  RRRRAVLTQKHKKKQSVLHLVPINITSK-DSDMTEVMWQPALRRGRGLEA  140

NP 003799.1       151 QGYGVRIQDAGVYLLYSQVLFQDVTFTMGQVVSR--EG-QGRQETLFRCI  197
NP 001192059.1    151 QGYGVRIQDAGVYLLYSQVLFQDVTFTMGQVVSR--EG-QGRQETLFRCI  197
NP 001192098.1    151 QGYVVRVWDSGIYLLYSQVLFHDVTFTMGQVVSR--EG-QGRQETLFRCI  197
NP 001029819.1    151 QGYVVRVWDAGVYLLYSQVLFHDETFTMGQMVSR--EG-QGRQETLFRCI  197
NP 076006.2       142 QGDIVRVWDTGIYLLYSQVLFHDVTFTMGQVVSR--EG-QGRRETLFRCI  188
NP 001009623.1    141 QGDTVRVRDTGIYLLYSQVLFHDVTFTMGQVVSR--EG-QGRRETLFRCI  187

NP 003799.1       198 RSMPSHPDRAYNSCYSAGVFHLHQGDILSVIIPRARAKLNLSPHGTFLGF  247
NP 001192059.1    198 RSMPSHPDRAYNSCYSAGVFHLHQGDILSVIIPRARAKLNLSPHGTFLGF  247
NP 001192098.1    198 RSMPSNPDWAYNSCYSAGVFHLHQGDILSVTIPRGRAKLSLSPHGTFLGF  247
NP 001029819.1    198 QSMPSNPDWAYNSCYSAGVFHLHQGDILSVVIPRARAKLSLSPHGTFLGL  247
NP 076006.2       189 RSMPSDPDRAYNSCYSAGVFHLHQGDIITVKIPRANAKLSLSPHGTFLGF  238
NP 001009623.1    188 KSMPSDPDRAYNSCYSAGVFHLHQGDIITVKIPRANAKLSLSPHGTFLGF  237

NP 003799.1          248   VKL   250   SEQ ID NO: 1
NP 001192059.1       248   VKL   250   SEQ ID NO: 4
NP 001192098.1       248   VKL   250   SEQ ID NO: 5
NP 001029819.1       248   VKL   250   SEQ ID NO: 6
NP 076006.2          239   VKL   241   SEQ ID NO: 7
NP 001009623.1       238   VKL   240   SEQ ID NO: 8
```

FIG. 5

```
NP 000591.1      1    MNSFSTSAFGPVAFSLGLLLVLPAAFPAPV       30
XP 518992.2      1    MNSVSTSAFGPVAFSLGLLLVLPAAFPAPV       30
NP 001036198.1   1    MNSFSTSAFGPVAFSLGLLLVLPAAFPAPV       30
NP 001003301.1   1    MNSLSTS-----AFSLGLLLVMATAFPTPG       25
NP 112445.1      1    MKFLSARDFHPVAF-LGLMLVTTTAFPTSQ       29
NP 036721.1      1    MKFLSARDFQPVAF-LGLMLLTATAFPTSQ       29

NP 000591.1      31   PPGEDSKDVAAPHRQPLTSSERIDKQIRYILDGISALRKETCNKS    75
XP 518992.2      31   PPGEDSKDVAAPHRQPLTSSERIDKQIRYILDGISALRKETCNKS    75
NP 001036198.1   31   LPGEDSKNVAAPHSQPLTSSERIDKHIRYILDGISALRKETCNRS    75
NP 001003301.1   26   PLAGDSKDDATSNSLPLTSANKVEELIKYILGKISALRKEMCDKF    70
NP 112445.1      30   VRRGDFTEDTTPNR-PVYTTSQVGGLITHVLWEIVEMRKELCNGN    73
NP 036721.1      30   VRRGDFTEDTTHNR-PVYTTSQVGGLITYVLREILEMRKELCNGN    73

NP 000591.1      76   NMCESSKEALAENNLNLPKMAEKDGCFQSGFNEETCLVKIITGLLEFEVY    125
XP 518992.2      76   NMCESSKEALAENNLNLPKMAEKDGCFQSGFNEETCLVKIITGLLEFEVY    125
NP 001036198.1   76   NMCESSKEALAENNLNLPKMAEKDGCFQSGFNEDTCLVKIITGLLEFEVY    125
NP 001003301.1   71   NKCEDSKEALAENNLHLPKLEGKDGCFQSGFNQETCLTRITTGLVEFQLH    120
NP 112445.1      74   SDCMNNDDALAENNLKLPEIQRNDGCYQTGYNQEICLLKISSGLLEYHSY    123
NP 036721.1      74   SDCMNSDDALSENNLKLPEIQRNDGCFQTGYNQEICLLKICSGLLEFRFY    123

NP 000591.1      126  LEYLQNRF-ESSEEQARAVQMSTKVLIQFLQKKAKNLDAITTPDPTTNAS    174
XP 518992.2      126  LEYLQNRF-ESSEEQARAVQMSTKVLIQFLQKKAKNLDAITTPDPTTNAS    174
NP 001036198.1   126  LEYLQNRF-ESSEEQARAVQMSTKVLIQFLQKKAKNLDAITTPEPTTNAS    174
NP 001003301.1   121  LNILQNNY-EGDKENVKSVHMSTKILVQMLKSKVKNQDEVTTPDPTTDAS    169
NP 112445.1      124  LEYMKNNLKDNKKDKARVLQRDTETLIHIFNQEVKDLHKIVLPTPISNAL    173
NP 036721.1      124  LEFVKNNLQDNKKDKARVIQSNTETLVHIFKQEIKDSYKIVLPTPTSNAL    173

NP 000591.1      175  LLTKLQAQNQWLQDMTTHLILRSFKEFLQSSLRALRQM   SEQ ID NO: 2
XP 518992.2      175  LLTKLQAQNQWLQDMTTHLILRSFKEFLQSSLRALRQM   SEQ ID NO: 9
NP 001036198.1   175  LLTKLQAQNQWLQDMTTHLILRSFKEFLQSNLRALRQM   SEQ ID NO: 10
NP 001003301.1   170  LQAILQSQDECVKHTTIHLILRSLEDFLQFSLRAVRIM   SEQ ID NO: 11
NP 112445.1      174  LTDKLESQKEWLRTKTIQFILKSLEEFLKVTLRSTRQT   SEQ ID NO: 12
NP 036721.1      174  LMEKLESQKEWLRTKTIQLILKALEEFLKVTMRSTRQT   SEQ ID NO: 13
```

FIG. 6

SEQUENCE LISTING

```
<160> NUMBER OF SEQ ID NOS: 13

<210> SEQ ID NO 1
<211> LENGTH: 250
<212> TYPE: PRT
<213> ORGANISM: Homo sapiens

<400> SEQUENCE: 1

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190
```

```
Leu Phe Arg Cys Ile Arg Ser Met Pro Ser His Pro Asp Arg Ala Tyr
            195                 200                 205

Asn Ser Cys Tyr Ser Ala Gly Val Phe His Leu His Gln Gly Asp Ile
        210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
            245                 250

<210> SEQ ID NO 2
<211> LENGTH: 212
<212> TYPE: PRT
<213> ORGANISM: Homo sapiens

<400> SEQUENCE: 2

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 3
<211> LENGTH: 135
<212> TYPE: PRT
<213> ORGANISM: Homo sapiens

<400> SEQUENCE: 3

Cys Glu Ser Ser Lys Glu Ala Leu Ala Glu Asn Asn Leu Asn Leu Pro
1               5                   10                  15

Lys Met Ala Glu Lys Asp Gly Cys Phe Gln Ser Gly Phe Asn Glu Glu
            20                  25                  30

Thr Cys Leu Val Lys Ile Ile Thr Gly Leu Leu Glu Phe Glu Val Tyr
        35                  40                  45
```

Leu Glu Tyr Leu Gln Asn Arg Phe Glu Ser Ser Glu Glu Gln Ala Arg
        50                  55                  60

Ala Val Gln Met Ser Thr Lys Val Leu Ile Gln Phe Leu Gln Lys Lys
65                  70                  75                  80

Ala Lys Asn Leu Asp Ala Ile Thr Thr Pro Asp Pro Thr Thr Asn Ala
                85                  90                  95

Ser Leu Leu Thr Lys Leu Gln Ala Gln Asn Gln Trp Leu Gln Asp Met
            100                 105                 110

Thr Thr His Leu Ile Leu Arg Ser Phe Lys Glu Phe Leu Gln Ser Ser
        115                 120                 125

Leu Arg Ala Leu Arg Gln Met
    130                 135

<210> SEQ ID NO 4
<211> LENGTH: 250
<212> TYPE: PRT
<213> ORGANISM: Pan troglodytes

<400> SEQUENCE: 4

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Arg Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 5
<211> LENGTH: 250
<212> TYPE: PRT

<213> ORGANISM: Canis lupus

<400> SEQUENCE: 5

Met Pro Ala Ser Ser Pro Ser Leu Leu Ala Pro Lys Gly Pro Pro Gly
1               5                   10                  15

Asp Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Asn Leu Arg Arg Glu Val Ala Arg
    50                  55                  60

Leu Gln Arg Thr Gly Gly Pro Ser Glu Lys Glu Gly Tyr Pro Trp
65                  70                  75                  80

Leu Ser Leu Gln Glu Gln Ser Pro Asp Ala Leu Glu Ala Trp Glu Asn
                85                  90                  95

Gly Glu Arg Ser Arg Arg Lys Arg Ala Ala Leu Ile His Lys Gln Lys
            100                 105                 110

Lys Lys His Ser Val Leu His Leu Val Pro Ile Asn Ile Thr Ser Lys
        115                 120                 125

Glu Asp Ser Asp Val Thr Glu Val Met Trp Gln Pro Ala Leu Lys Arg
    130                 135                 140

Gly Arg Gly Leu Glu Ala Gln Gly Tyr Val Val Arg Val Trp Asp Ser
145                 150                 155                 160

Gly Ile Tyr Leu Leu Tyr Ser Gln Val Leu Phe His Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser Asn Pro Asp Trp Ala Tyr
        195                 200                 205

Asn Ser Cys Tyr Ser Ala Gly Val Phe His Leu His Gln Gly Asp Ile
    210                 215                 220

Leu Ser Val Thr Ile Pro Arg Gly Arg Ala Lys Leu Ser Leu Ser Pro
225                 230                 235                 240

His Gly Thr Phe Leu Gly Phe Val Lys Leu
                245                 250

<210> SEQ ID NO 6
<211> LENGTH: 250
<212> TYPE: PRT
<213> ORGANISM: Bos taurus

<400> SEQUENCE: 6

Met Pro Ala Ser Ser Pro Ser Leu Leu Ser Pro Lys Gly Pro Gln Gly
1               5                   10                  15

Asp Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Val Leu
        35                  40                  45

Leu Thr Gln Gln Thr Glu Leu Gln Thr Leu Arg Arg Glu Val Thr Arg
    50                  55                  60

Leu Gln Arg Asn Gly Gly Pro Ser Glu Lys Gly Glu Gly Asn Pro Trp
65                  70                  75                  80

Leu Asn Leu Gln Glu Gln Ser Pro Asp Gly Thr Glu Gly Gln Glu Asn
                85                  90                  95

Gly Glu Arg Ser Arg Arg Arg Arg Ala Val Leu Thr Arg Lys His Lys

```
            100                 105                 110
Lys Lys Arg Ser Val Leu His Leu Val Pro Ile Asn Ile Thr Ser Lys
        115                 120                 125

Glu Asp Ser Asp Val Thr Glu Val Met Trp Gln Pro Ala Leu Gln Arg
    130                 135                 140

Gly Arg Gly Leu Glu Ala Gln Gly Tyr Val Arg Val Trp Asp Ala
145                 150                 155                 160

Gly Val Tyr Leu Leu Tyr Ser Gln Val Leu Phe His Asp Glu Thr Phe
                    165                 170                 175

Thr Met Gly Gln Met Val Ser Arg Glu Gly Gln Gly Arg Gln Glu Thr
            180                 185                 190

Leu Phe Arg Cys Ile Gln Ser Met Pro Ser Asn Pro Asp Trp Ala Tyr
        195                 200                 205

Asn Ser Cys Tyr Ser Ala Gly Val Phe His Leu His Gln Gly Asp Ile
    210                 215                 220

Leu Ser Val Val Ile Pro Arg Ala Arg Ala Lys Leu Ser Leu Ser Pro
225                 230                 235                 240

His Gly Thr Phe Leu Gly Leu Val Lys Leu
                    245                 250

<210> SEQ ID NO 7
<211> LENGTH: 241
<212> TYPE: PRT
<213> ORGANISM: Mus musculus

<400> SEQUENCE: 7

Met Pro Ala Ser Ser Pro Gly His Met Gly Gly Ser Val Arg Glu Pro
1               5                   10                  15

Ala Leu Ser Val Ala Leu Trp Leu Ser Trp Gly Ala Val Leu Gly Ala
            20                  25                  30

Val Thr Cys Ala Val Ala Leu Leu Ile Gln Gln Thr Glu Leu Gln Ser
        35                  40                  45

Leu Arg Arg Glu Val Ser Arg Leu Gln Arg Ser Gly Gly Pro Ser Gln
    50                  55                  60

Lys Gln Gly Glu Arg Pro Trp Gln Ser Leu Trp Glu Gln Ser Pro Asp
65                  70                  75                  80

Val Leu Glu Ala Trp Lys Asp Gly Ala Lys Ser Arg Arg Arg Ala
            85                  90                  95

Val Leu Thr Gln Lys His Lys Lys His Ser Val Leu His Leu Val
        100                 105                 110

Pro Val Asn Ile Thr Ser Lys Ala Asp Ser Asp Val Thr Glu Val Met
    115                 120                 125

Trp Gln Pro Val Leu Arg Arg Gly Arg Gly Leu Glu Ala Gln Gly Asp
130                 135                 140

Ile Val Arg Val Trp Asp Thr Gly Ile Tyr Leu Leu Tyr Ser Gln Val
145                 150                 155                 160

Leu Phe His Asp Val Thr Phe Thr Met Gly Gln Val Val Ser Arg Glu
                    165                 170                 175

Gly Gln Gly Arg Arg Glu Thr Leu Phe Arg Cys Ile Arg Ser Met Pro
            180                 185                 190

Ser Asp Pro Asp Arg Ala Tyr Asn Ser Cys Tyr Ser Ala Gly Val Phe
        195                 200                 205

His Leu His Gln Gly Asp Ile Ile Thr Val Lys Ile Pro Arg Ala Asn
    210                 215                 220
```

Ala Lys Leu Ser Leu Ser Pro His Gly Thr Phe Leu Gly Phe Val Lys
225                 230                 235                 240

Leu

<210> SEQ ID NO 8
<211> LENGTH: 240
<212> TYPE: PRT
<213> ORGANISM: Rattus norvegicus

<400> SEQUENCE: 8

Met Pro Ala Ser Ser Pro Gly Asn Met Gly Gly Ser Val Arg Glu Pro
1               5                   10                  15

Ala Leu Ser Val Thr Leu Trp Leu Ser Trp Gly Ala Val Leu Gly Ala
            20                  25                  30

Val Thr Cys Ala Val Ala Leu Leu Ile Gln Gln Ala Glu Leu Gln Ser
        35                  40                  45

Leu Arg Arg Glu Val Ser Arg Leu Gln Arg Ser Gly Gly Ala Ser Gln
    50                  55                  60

Lys Arg Gly Glu Pro Pro Trp Gln Ser Leu Trp Gln Ser Pro Asp
65                  70                  75                  80

Val Leu Gly Ala Trp Lys Asp Gly Ala Lys Ser Arg Arg Arg Ala
                85                  90                  95

Val Leu Thr Gln Lys His Lys Lys Gln Ser Val Leu His Leu Val
            100                 105                 110

Pro Ile Asn Ile Thr Ser Lys Asp Ser Asp Met Thr Glu Val Met Trp
        115                 120                 125

Gln Pro Ala Leu Arg Arg Gly Arg Gly Leu Glu Ala Gln Gly Asp Thr
    130                 135                 140

Val Arg Val Arg Asp Thr Gly Ile Tyr Leu Leu Tyr Ser Gln Val Leu
145                 150                 155                 160

Phe His Asp Val Thr Phe Thr Met Gly Gln Val Val Ser Arg Glu Gly
                165                 170                 175

Gln Gly Arg Arg Glu Thr Leu Phe Arg Cys Ile Lys Ser Met Pro Ser
            180                 185                 190

Asp Pro Asp Arg Ala Tyr Asn Ser Cys Tyr Ser Ala Gly Val Phe His
        195                 200                 205

Leu His Gln Gly Asp Ile Ile Thr Val Lys Ile Pro Arg Ala Asn Ala
    210                 215                 220

Lys Leu Ser Leu Ser Pro His Gly Thr Phe Leu Gly Phe Val Lys Leu
225                 230                 235                 240

<210> SEQ ID NO 9
<211> LENGTH: 212
<212> TYPE: PRT
<213> ORGANISM: Pan troglodytes

<400> SEQUENCE: 9

Met Asn Ser Val Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser

```
                65                  70                  75                  80
Ser Lys Glu Ala Leu Ala Glu Asn Asn Leu Asn Leu Pro Lys Met Ala
                    85                  90                  95
Glu Lys Asp Gly Cys Phe Gln Ser Gly Phe Asn Glu Glu Thr Cys Leu
                100                 105                 110
Val Lys Ile Ile Thr Gly Leu Leu Glu Phe Glu Val Tyr Leu Glu Tyr
                115                 120                 125
Leu Gln Asn Arg Phe Glu Ser Ser Glu Glu Gln Ala Arg Ala Val Gln
            130                 135                 140
Met Ser Thr Lys Val Leu Ile Gln Phe Leu Gln Lys Lys Ala Lys Asn
145                 150                 155                 160
Leu Asp Ala Ile Thr Thr Pro Asp Pro Thr Thr Asn Ala Ser Leu Leu
                165                 170                 175
Thr Lys Leu Gln Ala Gln Asn Gln Trp Leu Gln Asp Met Thr Thr His
                180                 185                 190
Leu Ile Leu Arg Ser Phe Lys Glu Phe Leu Gln Ser Ser Leu Arg Ala
                195                 200                 205
Leu Arg Gln Met
            210

<210> SEQ ID NO 10
<211> LENGTH: 212
<212> TYPE: PRT
<213> ORGANISM: Macaca mulatta

<400> SEQUENCE: 10

Met Asn Ser Phe Ser Thr Ser Ala Phe Gly Pro Val Ala Phe Ser Leu
1               5                   10                  15
Gly Leu Leu Leu Val Leu Pro Ala Ala Phe Pro Ala Pro Val Leu Pro
                20                  25                  30
Gly Glu Asp Ser Lys Asn Val Ala Ala Pro His Ser Gln Pro Leu Thr
                35                  40                  45
Ser Ser Glu Arg Ile Asp Lys His Ile Arg Tyr Ile Leu Asp Gly Ile
            50                  55                  60
Ser Ala Leu Arg Lys Glu Thr Cys Asn Arg Ser Asn Met Cys Glu Ser
65                  70                  75                  80
Ser Lys Glu Ala Leu Ala Glu Asn Asn Leu Asn Leu Pro Lys Met Ala
                    85                  90                  95
Glu Lys Asp Gly Cys Phe Gln Ser Gly Phe Asn Glu Asp Thr Cys Leu
                100                 105                 110
Val Lys Ile Ile Thr Gly Leu Leu Glu Phe Glu Val Tyr Leu Glu Tyr
                115                 120                 125
Leu Gln Asn Arg Phe Glu Ser Ser Glu Glu Gln Ala Arg Ala Val Gln
            130                 135                 140
Met Ser Thr Lys Val Leu Ile Gln Phe Leu Gln Lys Lys Ala Lys Asn
145                 150                 155                 160
Leu Asp Ala Ile Thr Thr Pro Glu Pro Thr Thr Asn Ala Ser Leu Leu
                165                 170                 175
Thr Lys Leu Gln Ala Gln Asn Gln Trp Leu Gln Asp Met Thr Thr His
                180                 185                 190
Leu Ile Leu Arg Ser Phe Lys Glu Phe Leu Gln Ser Asn Leu Arg Ala
                195                 200                 205
Leu Arg Gln Met
            210
```

<210> SEQ ID NO 11
<211> LENGTH: 207
<212> TYPE: PRT
<213> ORGANISM: Canis lupus

<400> SEQUENCE: 11

Met Asn Ser Leu Ser Thr Ser Ala Phe Ser Leu Gly Leu Leu Val
1               5                   10                  15

Met Ala Thr Ala Phe Pro Thr Pro Gly Pro Leu Ala Gly Asp Ser Lys
                20                  25                  30

Asp Asp Ala Thr Ser Asn Ser Leu Pro Leu Thr Ser Ala Asn Lys Val
            35                  40                  45

Glu Leu Ile Lys Tyr Ile Leu Gly Lys Ile Ser Ala Leu Arg Lys
50                  55                  60

Glu Met Cys Asp Lys Phe Asn Lys Cys Glu Asp Ser Lys Glu Ala Leu
65                  70                  75                  80

Ala Glu Asn Asn Leu His Leu Pro Lys Leu Glu Gly Lys Asp Gly Cys
                85                  90                  95

Phe Gln Ser Gly Phe Asn Gln Glu Thr Cys Leu Thr Arg Ile Thr Thr
            100                 105                 110

Gly Leu Val Glu Phe Gln Leu His Leu Asn Ile Leu Gln Asn Asn Tyr
        115                 120                 125

Glu Gly Asp Lys Glu Asn Val Lys Ser Val His Met Ser Thr Lys Ile
130                 135                 140

Leu Val Gln Met Leu Lys Ser Lys Val Lys Asn Gln Asp Glu Val Thr
145                 150                 155                 160

Thr Pro Asp Pro Thr Thr Asp Ala Ser Leu Gln Ala Ile Leu Gln Ser
                165                 170                 175

Gln Asp Glu Cys Val Lys His Thr Thr Ile His Leu Ile Leu Arg Ser
            180                 185                 190

Leu Glu Asp Phe Leu Gln Phe Ser Leu Arg Ala Val Arg Ile Met
        195                 200                 205

<210> SEQ ID NO 12
<211> LENGTH: 211
<212> TYPE: PRT
<213> ORGANISM: Mus musculus

<400> SEQUENCE: 12

Met Lys Phe Leu Ser Ala Arg Asp Phe His Pro Val Ala Phe Leu Gly
1               5                   10                  15

Leu Met Leu Val Thr Thr Thr Ala Phe Pro Thr Ser Gln Val Arg Arg
                20                  25                  30

Gly Asp Phe Thr Glu Asp Thr Thr Pro Asn Arg Pro Val Tyr Thr Thr
            35                  40                  45

Ser Gln Val Gly Gly Leu Ile Thr His Val Leu Trp Glu Ile Val Glu
50                  55                  60

Met Arg Lys Glu Leu Cys Asn Gly Asn Ser Asp Cys Met Asn Asn Asp
65                  70                  75                  80

Asp Ala Leu Ala Glu Asn Asn Leu Lys Leu Pro Glu Ile Gln Arg Asn
                85                  90                  95

Asp Gly Cys Tyr Gln Thr Gly Tyr Asn Gln Glu Ile Cys Leu Leu Lys
            100                 105                 110

Ile Ser Ser Gly Leu Leu Glu Tyr His Ser Tyr Leu Glu Tyr Met Lys
        115                 120                 125

```
                                  -continued

Asn Asn Leu Lys Asp Asn Lys Lys Asp Lys Ala Arg Val Leu Gln Arg
    130                 135                 140

Asp Thr Glu Thr Leu Ile His Ile Phe Asn Gln Glu Val Lys Asp Leu
145                 150                 155                 160

His Lys Ile Val Leu Pro Thr Pro Ile Ser Asn Ala Leu Leu Thr Asp
                165                 170                 175

Lys Leu Glu Ser Gln Lys Glu Trp Leu Arg Thr Lys Thr Ile Gln Phe
                180                 185                 190

Ile Leu Lys Ser Leu Glu Glu Phe Leu Lys Val Thr Leu Arg Ser Thr
                195                 200                 205

Arg Gln Thr
    210

<210> SEQ ID NO 13
<211> LENGTH: 211
<212> TYPE: PRT
<213> ORGANISM: Rattus norvegicus

<400> SEQUENCE: 13

Met Lys Phe Leu Ser Ala Arg Asp Phe Gln Pro Val Ala Phe Leu Gly
1               5                   10                  15

Leu Met Leu Leu Thr Ala Thr Ala Phe Pro Thr Ser Gln Val Arg Arg
                20                  25                  30

Gly Asp Phe Thr Glu Asp Thr Thr His Asn Arg Pro Val Tyr Thr Thr
            35                  40                  45

Ser Gln Val Gly Gly Leu Ile Thr Tyr Val Leu Arg Glu Ile Leu Glu
    50                  55                  60

Met Arg Lys Glu Leu Cys Asn Gly Asn Ser Asp Cys Met Asn Ser Asp
65                  70                  75                  80

Asp Ala Leu Ser Glu Asn Asn Leu Lys Leu Pro Glu Ile Gln Arg Asn
                85                  90                  95

Asp Gly Cys Phe Gln Thr Gly Tyr Asn Gln Glu Ile Cys Leu Leu Lys
                100                 105                 110

Ile Cys Ser Gly Leu Leu Glu Phe Arg Phe Tyr Leu Glu Phe Val Lys
                115                 120                 125

Asn Asn Leu Gln Asp Asn Lys Lys Asp Lys Ala Arg Val Ile Gln Ser
    130                 135                 140

Asn Thr Glu Thr Leu Val His Ile Phe Lys Gln Glu Ile Lys Asp Ser
145                 150                 155                 160

Tyr Lys Ile Val Leu Pro Thr Pro Thr Ser Asn Ala Leu Leu Met Glu
                165                 170                 175

Lys Leu Glu Ser Gln Lys Glu Trp Leu Arg Thr Lys Thr Ile Gln Leu
                180                 185                 190

Ile Leu Lys Ala Leu Glu Glu Phe Leu Lys Val Thr Met Arg Ser Thr
                195                 200                 205

Arg Gln Thr
    210
```

GROWTH AND SURVIVAL COMPOSITIONS FOR CELLS CAPABLE OF PRODUCING ANTIBODIES AND METHODS RELATED THERETO

CROSS-REFERENCE TO RELATED APPLICATIONS

This application is a division of U.S. application Ser. No. 15/735,933 filed Dec. 12, 2017 that granted as U.S. Pat. No. 11,124,766 on Sep. 21, 2021, which is the National Stage of International Application No. PCT/US2016/036650 filed Jun. 9, 2016, which claims the benefit of priority to U.S. Provisional Application Nos. 62/174,592 filed Jun. 12, 2015 and 62/328,439 filed Apr. 27, 2016. The entirety of each of these applications is hereby incorporated by reference for all purposes.

STATEMENT REGARDING FEDERALLY SPONSORED RESEARCH OR DEVELOPMENT

This invention was made with government support under AI121252 and AI078907 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 15057US ST25.txt. The text file is 26 KB, was created on Dec. 12, 2017, and is being submitted electronically via EFS-Web.

BACKGROUND

Human long-lived plasma cells (LLPCs) are responsible for the long-term maintenance of protective serum antibodies. However, the maintenance of LLPCs remain poorly understood. Plasma cells readily die when removed from their in vivo surrounding. Thus, there is a need to identify in vitro methods of inducing the replication or prolonging the survival of cells capable of producing antibodies.

Roldan et al. report VLA-4-fibronectin interaction is required for the terminal differentiation of human bone marrow cells capable of spontaneous and high rate immunoglobulin secretion. J Exp Med. 1992, 175(6):1739-47.

Minges Wols et al. report the role of bone marrow-derived stromal cells in the maintenance of plasma cell longevity. See Journal of immunology, 2002, 169, 4213-4221.

Cassese et al. report plasma cell survival is mediated by synergistic effects of cytokines and adhesion-dependent signals. Journal of immunology, 2003, 171, 1684-1690.

Mesin et al. report Long-lived plasma cells from human small intestine biopsies secrete immunoglobulins for many weeks in vitro. J Immunol. 2011, 187(6):2867-74.

Spencer et al. report the direct measurement of local oxygen concentration in the bone marrow of live animals. Nature. 2014, 508(7495):269-73.

Hallily et al. report long-lived plasma cells are contained within the CD19(−) CD38(hi)CD138(+) subset in human bone marrow. Immunity, 2015, 43(1):132-45.

References cited herein are not an admission of prior art.

SUMMARY

This disclosure relates to growth media and environments for in vitro culturing of cells that produce or are capable of producing antibodies. In certain embodiments, the media comprises IL-6, fibronectin, and typically a saccharide. In certain embodiments, the disclosure contemplates cell culture compositions comprising IL-6 and fibronectin that are derived from proteins secreted from mesenchymal stromal/stem cells (MSCs). In certain embodiments, the disclosure contemplates enclosures comprising culture compositions disclosed herein that are in ambient air or optionally in an environment wherein oxygen is absent or at a low concentration.

In certain embodiments, the enclosure comprises ambient air or is optionally sealed from the atmosphere wherein the amount of oxygen is less than 10%, 5.0%, 2.5%, 2.0%, 1.5%, 1.0%, 0.5%, or 0.1% by volume.

In certain embodiments, the proteins secreted from mesenchymal stem cells are derived from extracting the proteins from a group of mesenchymal stromal/stem cells (MSCs) or are derived from replicating or non-replicating mesenchymal stromal/stem cells (MSCs) or irradiated mesenchymal stromal/stem cells (MSCs) in the growth medium. In certain embodiments, the mesenchymal stem cells are grown to near confluence and irradiated.

In certain embodiments, the growth medium further comprises exogenously added APRIL, IL-6, and/or fibronectin. In certain embodiments, the growth media comprises the proteins interleukin-6 (IL-6) and fibronectin that are exogenously added. In certain embodiments, the growth media further comprises an exogenously added buffering agent, amino acids and vitamins. In certain embodiments, the growth media further comprises exogenously added blood. Typically, the blood is manipulated so that cells, platelets and/or clotting factor have been removed or are substantially absent, e.g., less than 5%, 3%, 2% or 1% by weight.

In certain embodiments, the disclosure relates to methods of culturing cells that are capable of producing antibodies comprising mixing cells capable of producing antibody with a cell growth medium disclosed herein. In certain embodiments, the cells that are capable of producing antibodies are plasma cells or antibody-secreting cells (ASCs). In certain embodiments, the plasma cells have surface molecules in a pattern wherein no or low levels of CD19 are expressed, CD138 is expressed, and CD38 is expressed in higher levels than CD138.

In certain embodiments, the culturing is done under conditions such that cells that are capable of producing and/or secreting antibodies survive or secret antibodies for more than 3, 4, 5, 6, 7, 8, 9, 10, 15, 20, 25, 30, 35, 40, 45, 50, 55, or 56 days.

In certain embodiments, the disclosure relates to composition comprising cells made by the process disclosed herein.

In certain embodiments, the disclosure contemplates the use of or secretions of allogeneic mesenchymal stromal/stem cells (MSCs) or syngeneic mesenchymal stromal/stem cells (MSCs). In certain embodiments, the disclosure contemplates that the growth medium does not contain syngeneic mesenchymal stromal/stem cells (MSCs). In certain embodiments, the disclosure contemplates that the cells capable of producing and/or antibody secreting cells have no cell to cell contact with the allogeneic mesenchymal stromal/stem cells (MSCs) or syngeneic mesenchymal stromal/stem cells (MSCs). In certain embodiments, the disclosure contemplates that the survival media comprises a product derived from the secreted products of allogeneic mesenchymal stromal/stem cells (MSCs). In certain embodiments, allogeneic mesenchymal stromal/stem cells (MSCs) or syngeneic mesenchymal stromal/stem cells (MSCs) are bone marrow derived mesenchymal stromal/stem cells (MSCs).

BRIEF DESCRIPTION OF THE SEVERAL VIEWS OF THE DRAWING(S)

FIG. 1A shows data on BM-MSC support for in vitro survival of blood ASC. Fresh sort-purified blood ASCs (CD19+CD27hiCD38hi) obtained from a healthy donor were cultured in RPMI with 10% Fetal bovine serum (conventional media: No MSC) or were co-cultured on allogeneic BM-MSCs (MSC). Cells were cultured 4 to 6 days. Each day, cells were harvested and frequency of IgG-secreting ASCs were measured by ELISpots and normalized to day 0 (100%). Co-cultures (day 1) of fresh sort-purified blood ASCs were obtained from a healthy subject 7 days after pneumococcal polysaccharide vaccine (PPSV23) and BM-MSCs (MSC).

Figure 1B:
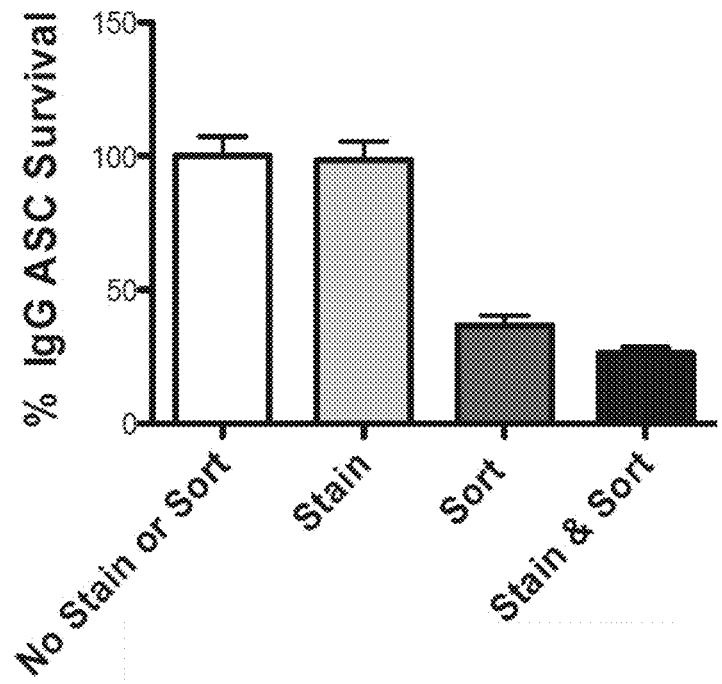

FIG. 1B shows data on the percentage of IgG ELISpot numbers of fresh untouched total peripheral blood mononuclear cells (PBMCs) (No Stain No Sort) (100%), PBMCs stained with the antibody panel only (Stain), PBMCs that were stressed with FAC sorting only (Sort), or PBMCs were stained with the antibody panel and FACS sorted (Stain & Sort). Each condition (untouched or stained and/or FAC sorted) with the same number of PBMC from a healthy donor. ELISpot wells shown. Flow cytometric analysis of Ki-67 expression of blood ASCs (CD19+CD27hiCD38hi) from a healthy subject was performed after 6 days after vaccination.

Figure 1C:
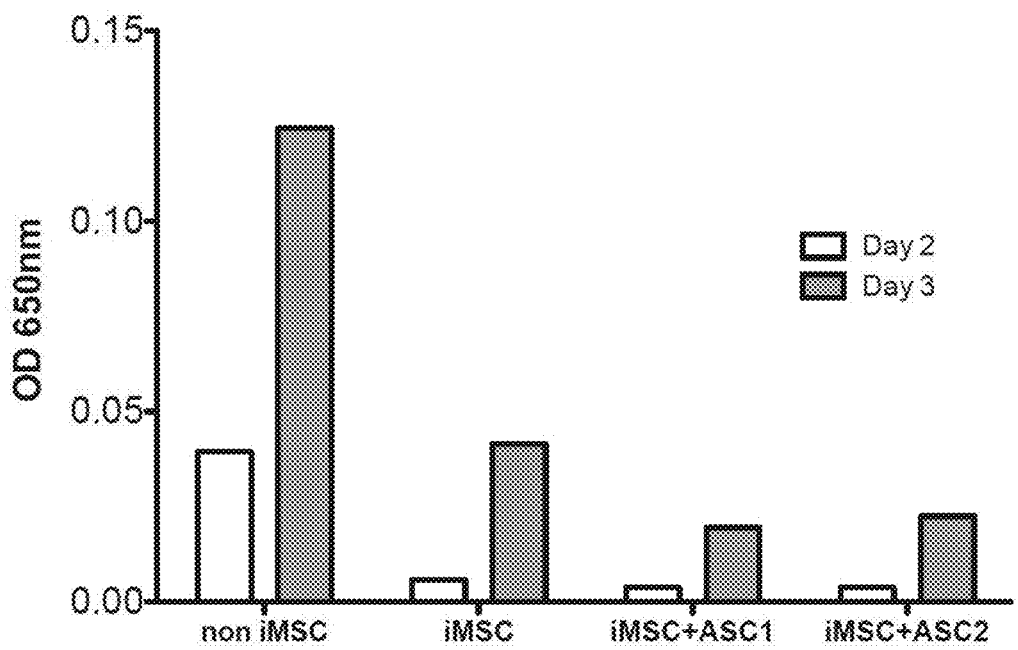

FIG. 1C shows data on BrdU incorporation at Day 2 (open bars) and Day 3 (filled bars) of the cultures of non-irradiated BM-MSCs (non-iMSC, 50,000 cells/well), irradiated BM-MSCs (iMSC,50,000 cells/well), FAC sorted blood ASCs from a healthy subject 11 days after multiple vaccines (at day 11 post-vaccination) (iMSC:ASC1, 50,000:500,000 cells/well), or FAC sorted ASCs from a second healthy subject 7 days after influenza-vaccinated (iMSC:ASC2 ratio, 50,000:500,000 cells/well).

Figure 1D:
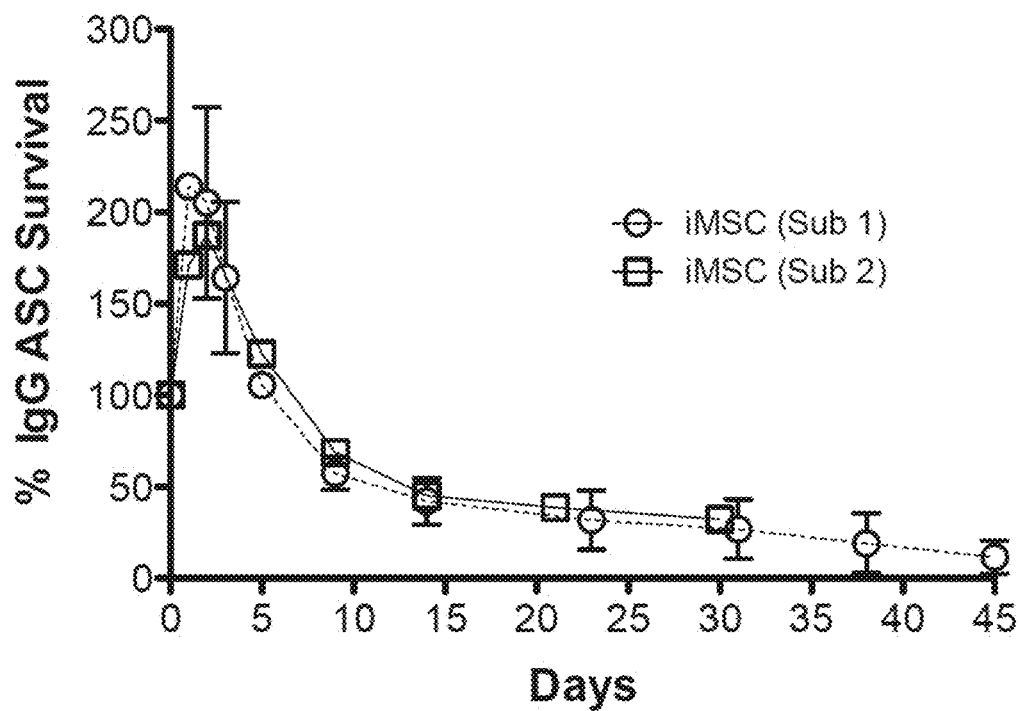

FIG. 1D shows data on FACS isolated ASCs from two healthy subjects and co-cultured with iMSC. One at steady state (ASC2) and one 8 days after Tdap (Tetanus, Diphtheria, Pertussis)-vaccinated (ASC1). Frequency of IgG-secreting ASCs (in percentage) by ELISpots for each indicated culture day was normalized to that of Day 0 (100%). Spots indicate viable IgG secreting cells on indicated culture day expressed in percentages of day 0 spots.

Figure 2:
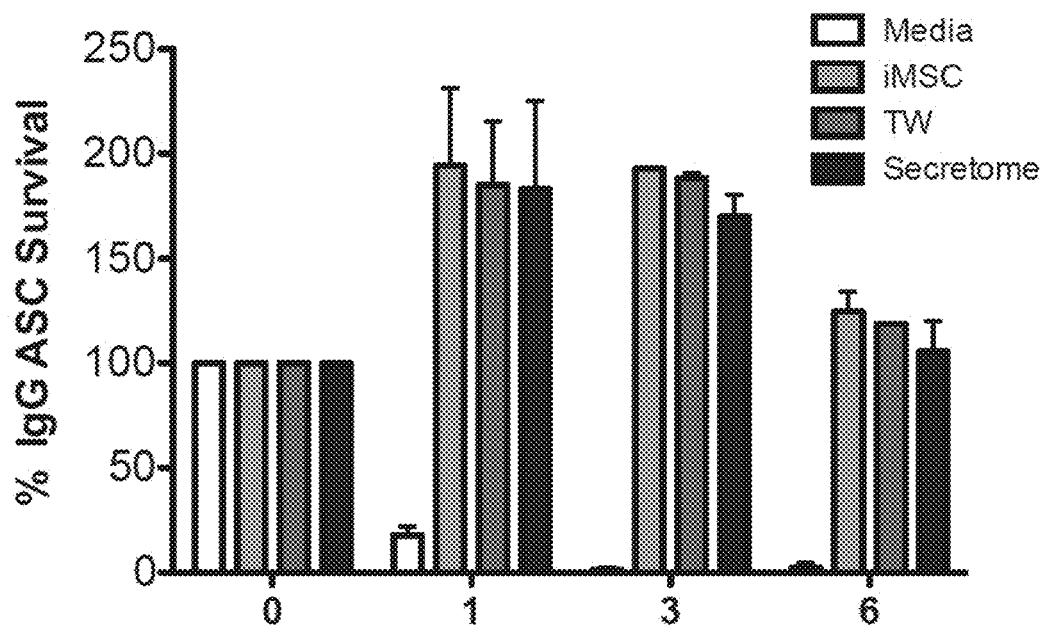

FIG. 2 data indicating pro-survival support of BM-MSC is independent of cell-cell contact. FACs purified blood ASCs 7 days after trivalent influenza virus or hepatitis vaccination) were cultured in R10 (Media alone), with MSCs, or in transwells with ASC and MSC or with MSC secretome. Frequency of IgG-secreting ASCs (in percentage) for each indicated culture day was normalized to Day 0. Results are expressed as the mean percentage of viable cell counts. ELISpot scanned images were obtained from the experiments (ASC from hepatitis B-vaccinated).

Figure 3:
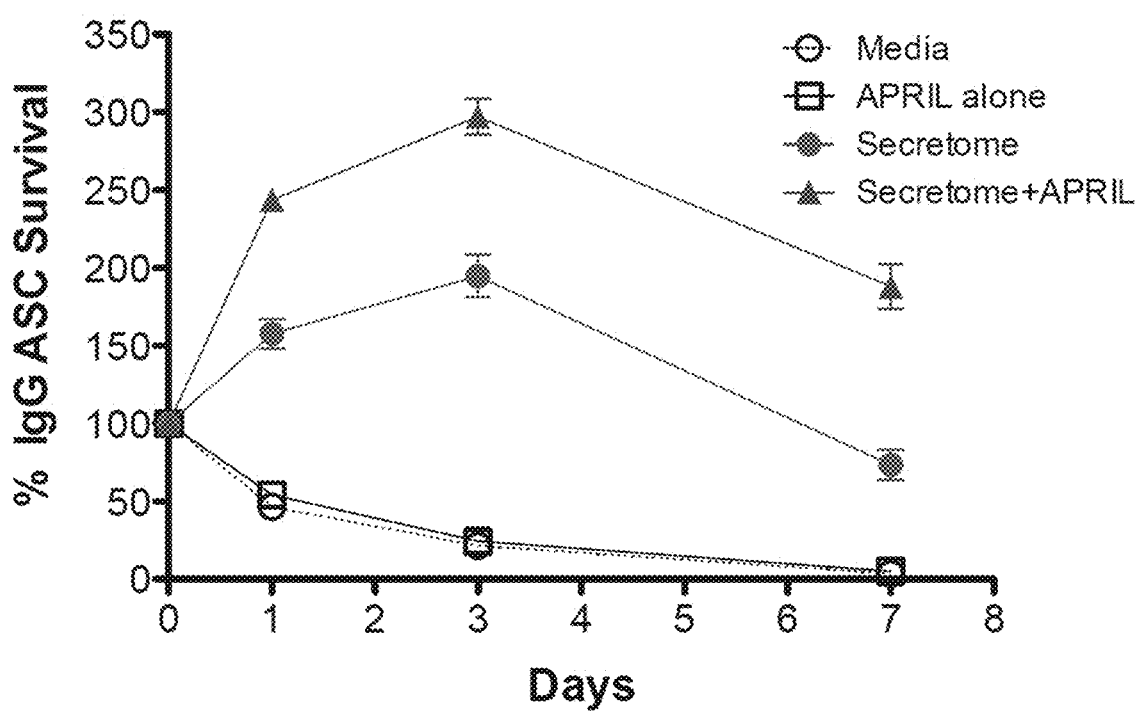

FIG. 3 shows data indicating in vitro survival of blood ASC with the secretome and exogenous APRIL. ASC sort purified from blood of an adult 7 days post-influenza-vaccination cultured in media alone (RPMI with 10% FBS) (open circles), with Media+APRIL (open squares), with secretome alone (circles), with secretome and APRIL (red triangles). Frequency of IgG-secreting ASC (in percentage) normalized to Day 0. Results are expressed as the mean percentage of spots from day 0. ELISpot images were taken from days 0, 1, 3, and 7 days in culture. ASC sort purified from healthy adults were taken at steady state or various vaccinated donors (PPSV, tetanus, influenza, and MMR) were cultured in media alone, secretome alone, or secretome and APRIL.

Figure 4A:
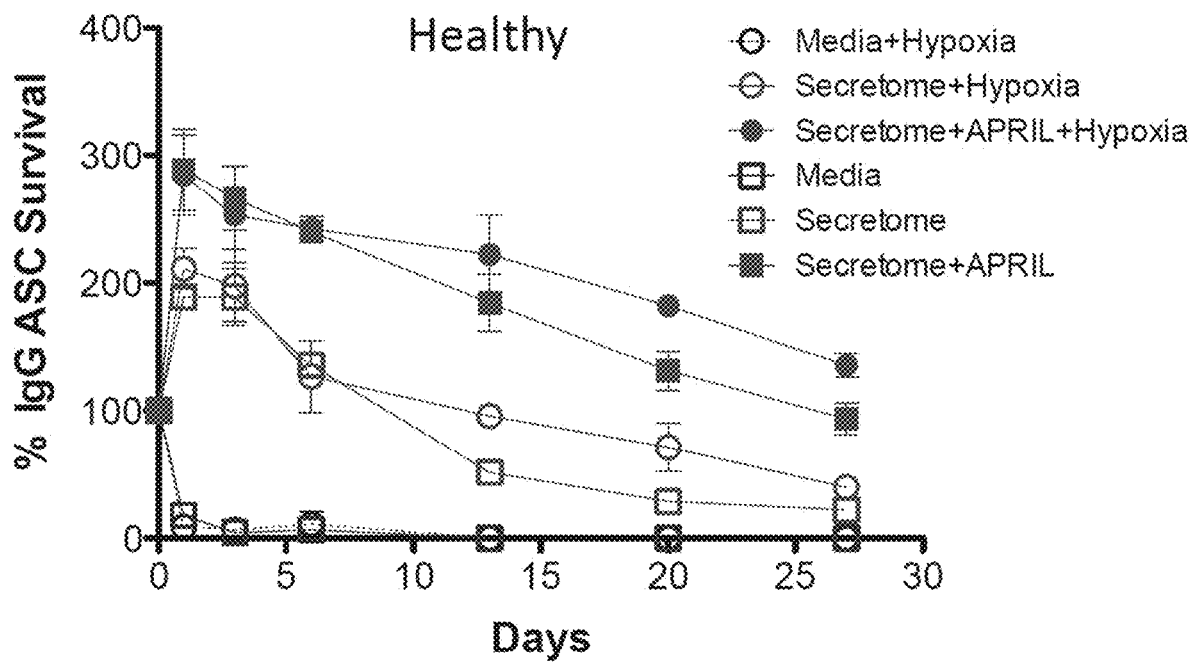

FIG. 4A shows data on in vitro survival of blood ASC is enhanced by hypoxic conditions. Fresh sort-purified blood ASC a healthy adult at steady state were cultured in secretome alone in normoxia or hypoxia or secretome with APRIL in normoxia or in hypoxia, and representative IgG ELISpots on day 1 through 27 were evaluated. Cultures of ASC in normoxia from media alone, secretome alone or secretome and APRIL. Cultures of ASC in hypoxia from media alone secretome alone or secretome and APRIL. Percentage of IgG ELISpots normalized to day 0.

Figure 4B:
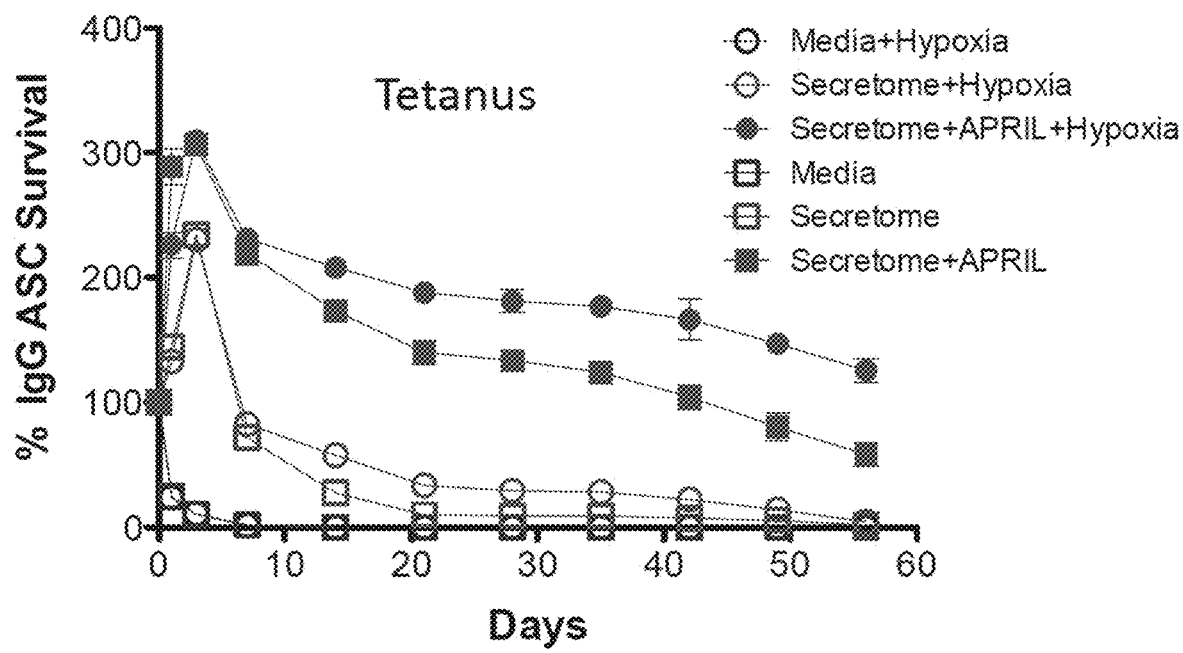

FIG. 4B shows data on circulating ASC 7 days after tetanus vaccination from a healthy adult which were cultured in secretome alone in normoxia or hypoxia or secretome with APRIL in normoxia or in hypoxia. Representative IgG ELISpots were obtained from day 1 through 56 of cultures. Percentage of IgG ELISpots normalized to day 0 are shown on graph. Cultures of ASC in normoxia from media alone, secretome alone or secretome and APRIL. Cultures of ASC in hypoxia from media alone secretome alone or secretome and APRIL.

FIG. 5 shows a sequence comparison of APRIL (TNFSF13), NP 003799.1 (SEQ ID NO: 1) for *H. sapiens*; NP_001192059.1 (SEQ ID NO: 4) for *P. troglodytes* (99% identity to human); NP_001192098.1 (SEQ ID NO: 5) for *C. lupus* (87% identity); NP_001029819.1 (SEQ ID NO: 6) for *B. taurus* (84% identity); NP_076006.2 (SEQ ID NO: 7) for *M. musculus* (81% identity); NP_001009623.1 (SEQ ID NO: 8) for *R. norvegicus* (80%).

FIG. 6 shows a sequence comparison of IL6, NP_000591.1 (SEQ ID NO: 2) for *H. sapiens*; XP_518992.2 (SEQ ID NO: 9) for *P. troglodytes* (99% identity to human); NP_001036198.1 (SEQ ID NO: 10) for *M. mulatta* (96% identity); NP_001003301.1 (SEQ ID NO: 11) for *C. lupus* (54%); NP_112445.1(SEQ ID NO: 12) for *M. musculus* (40%); NP_036721.1 (SEQ ID NO: 13) for *R. norvegicus* (41%).

DETAILED DISCUSSION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

The term "mesenchymal stromal cells" refers to the subpopulation of fibroblast or fibroblast-like nonhematopoietic cells with properties of plastic adherence and capable of in vitro differentiation into cells of mesodermal origin which may be derived from bone marrow, adipose tissue, umbilical cord (Wharton's jelly), umbilical cord perivascular cells, umbilical cord blood, amniotic fluid, placenta, skin, dental pulp, breast milk, and synovial membrane, e.g., fibroblasts or fibroblast-like cells with a clonogenic capacity that can differentiate into several cells of mesodermal origin, such as adipocytes, osteoblasts, chondrocytes, skeletal myocytes, or visceral stromal cells. The term, "mesenchymal stem cells" refers to the cultured (self-renewed) progeny of primary mesenchymal stromal cell populations. Mesenchymal stromal/stem cells (MSCs) refers to mesenchymal stromal and/or mesenchymal stem cells.

Bone marrow derived mesenchymal stromal cells are typically expanded ex vivo from bone marrow aspirates to confluence. Certain mesenchymal stromal/stem cells (MSCs) share a similar set of core markers and properties. Certain mesenchymal stromal/stem cells (MSCs) may be defined as positive for CD105, CD73, and CD90 and negative for CD45, CD34, CD14 or CD11b, CD79α or CD19, and HLA-DR surface markers, and have the ability to adhere to plastic. See Dominici et al. Minimal criteria for defining multipotent mesenchymal stromal cells. The International Society for Cellular Therapy position statement. Cytotherapy. 2006, 8(4):315-7.

Plasma cells (PCs) in human BM express high amounts of CD38. Long lived plasma cells can be obtained from human bone marrow cells, e.g., from iliac crest aspirates. Cells may be separated by flow cytometry. One can us FACS to remove lymphocytes having CD3 or CD14 expression (non-T cells, non-monocytes) and IgD cells (to eliminate late transitional and naive B cells). The remaining cells may be divided remove CD19 cell populations and subsequently obtained by the expression of both CD138 and CD38. In certain embodiments, antibody secreting cells such as ACSs or PC provide immunoglobulin secretion of at or more than 100, 125, 150 or 167±23 pg/cell/day.

The term "fluorescence-activated cell sorting" or "FACS" refers to a method of sorting a mixture of cells into two or more areas, typically one cell at a time, based upon the fluorescent characteristics of each cell. It is typically accomplished by applying an electrical charge and separating by movement through an electrostatic field. Fluorescent antibodies with epitopes to cell surface markers can be mixed with cells to mark the cells or cells can be transfected with fluorescent probes or molecular beacons that bind to mRNA. Typically, in FACS, a vibrating mechanism causes a stream of cells to break into individual droplets. Just prior to droplet formation, cells in a fluid pass through an area for measuring fluorescence of the cell. An electrical charging mechanism is configured at the point where the stream breaks into droplets. Based on the fluorescence intensity measurement, a respective electrical charge is imposed on the droplet as it breaks from the stream. The charged droplets then move through an electrostatic deflection system that diverts droplets into areas based upon their relative charge. In some systems, the charge is applied directly to the stream, and the droplet breaking off retains charge of the same sign as the stream. In other systems, a charge is provided on a conduit inducing an opposite charge on the droplet.

"Fibronectin" refers to either plasma insoluble fibronectin typically produced by fibroblasts, e.g., in an extracellular matrix, and plasma soluble fibronectin produced in the liver by hepatocytes sometimes referred to as "cold-insoluble globulin" which is a protein component of blood plasma. Fibronectin exists as a protein dimer, consisting of two monomers linked near the C-terminus by a pair of disulfide bonds. A typical fibronectin contains 12 type I modules, 2 type II modules, and 15-17 type III modules. The number of modules varies based on alternative gene splicing. There are two alternatively spliced segments in fibronectin due to alternative exon usage: extra domain A (EDA) located between the 11th and 12th of type III modules, and extra domain B (EDB) between the seventh and eighth type III modules. Plasma fibronectin typically lacks EDA and EDB sequences.

In certain embodiments, a growth medium disclosed herein comprises exogenously added fibronectin, fragment, or variant thereof. In certain embodiments, fibronectin is in the growth medium at a concentration of greater than $0.001 \times 10^{-3}\%$, $0.002 \times 10^{-3}\%$, $0.003 \times 10^{-3}\%$, $0.004 \times 10^{-3}\%$, $0.005 \times 10^{-3}\%$, $0.007 \times 10^{-3}\%$, $0.010 \times 10^{-3}\%$, $0.020 \times 10^{-3}\%$, $0.030 \times 10^{-3}\%$, $0.050 \times 10^{-3}\%$, $0.10 \times 10^{-3}\%$, $0.20 \times 10^{-3}\%$, $0.30 \times 10^{-3}\%$, $0.50 \times 10^{-3}\%$, $1.0 \times 10^{-3}\%$, $1.5 \times 10^{-3}\%$, $2.0 \times 10^{-3}\%$, 0.001%, 0.002%, 0.003%, 0.004%, 0.005%, 0.007%, 0.010%, 0.020%, 0.030%, 0.050%, 0.10%, 0.20%, 0.30%, 0.50%, 1.0%, 1.5%, 2.0%, by weight.

The protein "APRIL" refers to tumor necrosis factor superfamily member 13, which is a ligand for B-cell maturation antigen, a member of the tumor necrosis factor (TNF) receptor family. In certain embodiments, a growth medium disclosed herein comprises exogenously added APRIL, fragment, or variant thereof. In certain embodiments, the variant has greater than 30, 40, 50, 60, 70, 80, 85, 90, 95, 96, 97, 98 or 99% identity or similarity to (SEQ ID NO: 1)

MPASSPFLLAPKGPPGNMGGPVREPALSVALWLSWGAALGAVACAMALLTQ

QTELQSLRREVSRLQGTGGPSQNGEGYPWQSLPEQSSDALEAWENGERSRK

RRAVLTQKQKKQHSVLHLVPINATSKDDSDVTEVMWQPALRRGRGLQAQGY

-continued

GVRIQDAGVYLLYSQVLFQDVTFTMGQVVSREGQGRQETLFRCIRSMPSHP

DRAYNSCYSAGVFHLHQGDILSVIIPRARAKLNLSPHGTFLGFVKL.

In certain embodiments, APRIL is in the growth medium at a concentration of greater than $0.001 \times 10^{-3}$%, $0.002 \times 10^{-3}$%, $0.003 \times 10^{-3}$%, $0.004 \times 10^{-3}$%, $0.005 \times 10^{-3}$%, $0.007 \times 10^{-3}$%, $0.010 \times 10^{-3}$%, $0.020 \times 10^{-3}$%, $0.030 \times 10^{-3}$%, $0.050 \times 10^{-3}$%, $0.10 \times 10^{-3}$%, $0.20 \times 10^{-3}$%, $0.30 \times 10^{-3}$%, $0.50 \times 10^{-3}$%, $1.0 \times 10^{-3}$%, $1.5 \times 10^{-3}$%, $2.0 \times 10^{-3}$%, 0.001%, 0.002%, 0.003%, 0.004%, 0.005%, 0.007%, 0.010%, 0.020%, 0.030%, 0.050%, 0.10%, 0.20%, 0.30%, 0.50%, 1.0%, 1.5%, 2.0%, by weight.

In response to injury, inflammatory cells such as neutrophil granulocytes and macrophages secrete a number of cytokines, most notable of which are the interleukins IL-1, IL-6 and IL-8, and TNFα. "IL-6" refers to the Interleukin-6 protein. IL-6 signals through a cell-surface type I cytokine receptor complex consisting of the ligand-binding IL-6Rα chain (CD126), and the signal-transducing component gp130 (CD130). IL-6 is thought to be involved in the activation of the immune system, regenerative processes, and regulation of metabolism.

In certain embodiments, a growth medium disclosed herein comprises exogenously added IL-6, fragment, or variant thereof. In certain embodiments, the variant has greater than 30, 40, 50, 60, 70, 80, 85, 90, 95, 96, 97, 98 or 99% identity or similarity to isoform 1 (SEQ ID NO: 2)

MNSFSTSAFGPVAFSLGLLLVLPAAFPAPVPPGEDSKDVAAPHRQPLTSSE

RIDKQIRYILDGISALRKETCNKSNMCESSKEALAENNLNLPKMAEKDGCF

QSGFNEETCLVKIITGLLEFEVYLEYLQNRFESSEEQARAVQMSTKVLIQF

LQKKAKNLDAITTPDPTTNASLLTKLQAQNQWLQDMTTHLILRSFKEFLQS

SLRALRQM.

In certain embodiments, the variant has greater than 30, 40, 50, 60, 70, 80, 85, 90, 95, 96, 97, 98 or 99% identity or similarity to isoform 2 (SEQ ID NO: 3),

CESSKEALAENNLNLPKMAEKDGCFQSGFNEETCLVKIITGLLEFEVYLEY

LQNRFESSEEQARAVQMSTKVLIQFLQKKAKNLDAITTPDPTTNASLLTKL

QAQNQWLQDMTTHLILRSFKEFLQSSLRALRQM.

In certain embodiments, IL-6 is in the growth medium at a concentration of greater than $0.001 \times 10^{-3}$%, $0.002 \times 10^{-3}$%, $0.003 \times 10^{-3}$%, $0.004 \times 10^{-3}$%, $0.005 \times 10^{-3}$%, $0.007 \times 10^{-3}$%, $0.010 \times 10^{-3}$%, $0.020 \times 10^{-3}$%, $0.030 \times 10^{-3}$%, $0.050 \times 10^{-3}$%, $0.10 \times 10^{-3}$%, $0.20 \times 10^{-3}$%, $0.30 \times 10^{-3}$%, $0.50 \times 10^{-3}$%, $1.0 \times 10^{-3}$%, $1.5 \times 10^{-3}$%, $2.0 \times 10^{-3}$%, 0.001%, 0.002%, 0.003%, 0.004%, 0.005%, 0.007%, 0.010%, 0.020%, 0.030%, 0.050%, 0.10%, 0.20%, 0.30%, 0.50%, 1.0%, 1.5%, 2.0%, by weight.

Sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example the polypeptides GGGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q.

As used herein a "growth medium" or "media" refers to a composition that contains components, such as vitamins, amino acids, inorganic salts, a buffer, and a fuel, e.g., acetate, succinate, and/or a saccharide, that support the growth and maintenance of cell lines. Components in the growth medium may be derived from blood serum or the growth medium may be serum-free. The growth medium may optionally be supplemented with albumin, lipids, insulin and/or zinc, transferrin or iron, selenium, ascorbic acid, and an antioxidant such as glutathione, 2-mercaptoethanol or 1-thioglycerol.

As used herein the term "allogeneic" with regard to comparing cells capable of and/or secreting antibodies and mesenchymal stromal/stem cells (MSCs) refers to cells that are genetically dissimilar because they are not derived from the same person, e.g., the antibody secreting cells and the mesenchymal stromal/stem cells (MSCs), which provide for proteins secreted from mesenchymal stromal/stem cells (MSCs) in a growth media, are not both derived from the same person. Cells derived from the same person are designated as "syngeneic."

In certain embodiments, the disclosure contemplates a growth media disclosed herein having one or more of the following components the RPMI 1640 and R10 medium at, about, or greater than those provided in the tables herein. The term "about" refers to having more or less not exceeding 10, 20, 30, 40 or 50% by weight.

RPMI 1640 Medium contains the reducing agent glutathione and vitamins. RPMI 1640 Medium contains biotin, vitamin B12, and PABA. In addition, the vitamins inositol and choline are present. RPMI 1640 Medium does not contain substantial amounts of proteins, lipids, or growth factors. RPMI 1640 Medium is commonly supplemented with 1-5% or 5-10% Fetal Bovine Serum (FBS). RPMI 1640 Medium uses a sodium bicarbonate buffer system (2.0 g/L).

TABLE 1

| Components RPMI 1640 Medium | | |
|---|---|---|
| | Molecular Weight | Concentration (mg/L) |
| Amino Acids | | |
| Glycine | 75.0 | 10.0 |
| L-Arginine | 174.0 | 200.0 |
| L-Asparagine | 132.0 | 50.0 |
| L-Aspartic acid | 133.0 | 20.0 |
| L-Cystine 2HCl | 313.0 | 65.0 |
| L-Glutamic Acid | 147.0 | 20.0 |
| L-Glutamine | 146.0 | 300.0 |
| L-Histidine | 155.0 | 15.0 |
| L-Hydroxyproline | 131.0 | 20.0 |
| L-Isoleucine | 131.0 | 50.0 |
| L-Leucine | 131.0 | 50.0 |
| L-Lysine hydrochloride | 183.0 | 40.0 |
| L-Methionine | 149.0 | 15.0 |
| L-Phenylalanine | 165.0 | 15.0 |

TABLE 1-continued

Components RPMI 1640 Medium

|  | Molecular Weight | Concentration (mg/L) |
|---|---|---|
| L-Proline | 115.0 | 20.0 |
| L-Serine | 105.0 | 30.0 |
| L-Threonine | 119.0 | 20.0 |
| L-Tryptophan | 204.0 | 5.0 |
| L-Tyrosine disodium salt dihydrate | 261.0 | 29.0 |
| L-Valine | 117.0 | 20.0 |
| Vitamins |  |  |
| Biotin | 244.0 | 0.2 |
| Choline chloride | 140.0 | 3.0 |
| D-Calcium pantothenate | 477.0 | 0.25 |
| Folic Acid | 441.0 | 1.0 |
| Niacinamide | 122.0 | 1.0 |
| Para-Aminobenzoic Acid | 137.0 | 1.0 |
| Pyridoxine hydrochloride | 206.0 | 1.0 |
| Riboflavin | 376.0 | 0.2 |
| Thiamine hydrochloride | 337.0 | 1.0 |
| Vitamin $B_{12}$ | 1355.0 | 0.005 |
| i-Inositol | 180.0 | 35.0 |
| Inorganic Salts |  |  |
| Calcium nitrate $(Ca(NO_3)_2\ 4H_2O)$ | 236.0 | 100.0 |
| Magnesium Sulfate $(MgSO_4)$ (anhyd.) | 120.0 | 48.84 |
| Potassium Chloride (KCl) | 75.0 | 400.0 |
| Sodium Bicarbonate $(NaHCO_3)$ | 84.0 | 2000.0 |
| Sodium Chloride (NaCl) | 58.0 | 6000.0 |
| Sodium Phosphate dibasic $(Na_2HPO_4)$ anhydrous | 142.0 | 800.0 |
| Other Components |  |  |
| D-Glucose (Dextrose) | 180.0 | 2000.0 |
| Glutathione (reduced) | 307.0 | 1.0 |
| Phenol Red | 376.4 | 5.0 |
| R10 medium |  |  |

500 mL, RPMI 1640 medium
55 mL Heat-inactivated
fetal calf serum (FCS)
5 mL, L-glutamine
(200 mM solution)
5 mL, Penicillin/streptomycin
(10,000 U per mL
and 10 mg per mL)
5 mL 1M HEPES buffer Other contemplated components in these growth medium include ascorbic acid, L-alanine, zinc sulfate, human transferrin, albumin, insulin, ammonium metavanadate, cupric sulfate, manganous chloride, sodium selenite, ethanolamine, and sodium pyruvate.

The term "saccharide" refers to multi-hydroxylated hydrocarbons which predominantly form one or more cyclic five and/or six membered nonaromatic oxygen containing cyclic isomers in aqueous solutions. The term includes monosaccharides, disaccharides, or polysaccharides such as glucose, dextrose, fructose, lactose, mannose, sorbitol, or sucrose.

The term, "irradiation" of the cells, refers to exposing the cells to a γ-irradiation source. In certain embodiments, one irradiates the cells at about or more than or 50, 60, 70, 75 or 76.6 rad/minute (e.g. ~0.766 Gy/minute) and do so for at or more than 20, 25, 30, 35 or 40 minutes. ~3,064 rad, or ~30.64 Gy).

Antibody Secreting Cell (ASC) Survival

Human plasma cells (PCs), or antibody-secreting cells (ASCs), produce antibodies (Abs) that provide protection from infections. As terminally-differentiated cells, these cells rapidly die in conventional ex vivo cultures. This hinders in vitro studies of these 1 immune cells. It may be that bone marrow (BM)-derived mesenchymal stromal cells (MSCs) "microniches" where long-lived PCs reside, prolong ASC survival in vitro. To test this hypothesis, peripheral blood (PB) ASCs were cultured on BM-MSCs and their survival and Ab production were assessed by ELISpot and ELISA assays. ASCs died within 1-3 days in conventional cultures; however, when co-cultured with BM-MSCs, they survived and continuously secreted Abs for greater than 63 days. MSC-ASC cell-cell contact was not necessary. BM-MSC secretome supported ASC survival similarly. APRIL alone did not support ASC survival, but APRIL together with BM-MSC secretome promoted survival and Ab secretion of cultured ASCs. In addition, ASCs cultured with APRIL in BM-MSC secretome in hypoxia (2.5% 02) showed enhanced cell survival compared to those in normoxic conditions (for greater than 56 days). The human secretome from BM-MSCs supports long-term (more than a month) ex vivo survival and Ab production of human PB ASCs. These paracrine effects were further enhanced by exogenous APRIL and hypoxic stress.

Circulating ASC upon arrival to the hypoxic BM microniche require the paracrine survival factors from the BM stroma and APRIL from eosinophils or neutrophils to maintain survival. Serendipitously methods were developed to understand additional mechanisms of plasma cell differentiation and maintenance. These can be used as tools for basic plasma cell biology central to advance fields of vaccinology, oncology, autoimmunity, allergy, and transplantation.

The BM microenvironment is important for plasma cells (PCs). Experiments indicate that amidst the sundry collection of cells, the BM-MSC is necessary but not sufficient for human plasma cell survival. Human PCs in both in vitro and animal models suggested that MSC effects were mediated by both cell-to-cell contact and soluble factors. Proximity of the MSC to the plasma cell is paramount with local concentration of survival factors but cell-to-cell contact is not necessary. Thus, allogeneic human MSC secretome provided a full collection of plasma cell survival factors.

Although the BM-MSC are necessary, they alone were not sufficient to sustain long-term plasma cell survival. The synergistic effect of one cytokine, APRIL, together with the BM MSC secretome prolonged survival as well as increased Ig production per cell as shown by the size of the ELISpots. These studies indicate that MSC do not readily provide APRIL in the BM microniche or at least not in meaningful abundance. Finally, plasma cells in the MSC secretome in hypoxia were maintained longer than in normoxia. Thus, the MSC survival media with APRIL in hypoxia enhanced long-lived survival of blood ASC for almost 2 months and likely could be sustained longer. These differences were not immediate but with survival curves diverging after 7 days depicted intrinsic changes of the plasma cell imparted by the unique features and special secreted factors provided by the BM microniche.

Plasma cells are terminally differentiated professional antibody secreting factories. Yields of viable human ASC are diminished after surface staining in the cold combined with sorting under high-pressure flow systems. However, culture conditions disclosed herein increased cell numbers of IgG ASC on 1-2 days. Although, this phenomenon could have been due to proliferation of blood ASC, no proliferation is detected by BrdU labeling of Ki67+ cells. Thus, Ki67+ staining of these cells are a result of recent proliferation and not ongoing cell division. Thus, FACS sorted ASC are re-awakened from a "non-secreting" to a fully active "secreting" phenotype. Hence, immunoglobulin secretion is not entirely constitutive but is modulated during stress and revived during nutrient rich states.

Nearly all ASC in the blood are positive for Ki67 staining which was originally interpreted as ongoing division of plasmablasts even after upregulation of BLIMP-1. However, BLIMP-1 expression has been shown to repress c-myc and other genes involved in cell cycle progression and cell division suggesting plasma cell differentiation programs are distinct from proliferation. ASC positive for Ki67+, a marker of ribosomal RNA localized to the nucleus during interphase, are not actively proliferating but rather have undergone recent proliferation.

APRIL is secreted by eosinophils and neutrophils which are found in the BM. Eosinophils are important in LLPC generation and maintenance. APRIL played an additive role in long-term plasma cell survival in the presence of the BM-MSC secretome demonstrating that APRIL was not provided by the BM-MSC. Proximity of eosinophils and plasma cells was thought to be essential due to the importance of cell-to-cell contact. However, exogenous APRIL within the BM microsite is important for long-term ASC survival and eosinophil-plasma cell contact was not necessary. Eosinophils have also been shown to be important in the generation of IgA plasma cells. However, a higher frequency of IgG plasma cells are found in the BM LLPC compartment (CD19-CD38hiCD138+) compared to IgA plasma cells. Interestingly, in vitro BM microniche cultures, IgA ASC were not "revived" on days 1-2. Even with APRIL and the BM secretome, IgA ASC gradually waned after 2 weeks. Thus, this in vitro BM plasma cell survival system is optimal for IgG plasma cells and a different potpourri of factors will likely be central for IgA plasma cell survival.

The circulating ASC are easily found in blood after immunization and infection and many undergo apoptosis since serum antibody peak by one month and quickly decline within 2-3 months. The sustained secondary serum antibody kinetics are likely due to those circulating ASC that have migrated to survival sites in the human BM in proximity to the MSC and APRIL enriched zones. Our studies demonstrate that the BM microniche not only supports plasma cells but likely alters its phenotype to adapt to hostile hypoxic sites. Our RNA transcriptome analysis of ex vivo BM plasma cell populations (both short-lived and long-lived) suggest upregulation of hypoxia adaptation pathways, altered metabolic pathways, and autophagy pathways.

Reaction of the GC is important in generating LLPC, however, it is unclear if a unique subset of post-GC circulating ASC are intrinsically programmed to be LLPC such as CD138+ subset of blood ASC. One model proposes that all circulating ASC have the potential to become LLPC, provided they undergo each sequential differentiation step such as upregulation of CD38, CD27, CD138, and eventual loss of CD19 to become LLPC.

As an example, ASC from the patient who received the PSV23 had only a frequency of 70% of total ASC survival on day 8 in MSC secretome and APRIL compared to other vaccine responses with over 180% survival on day 6-8. Moreover, the high frequency of plasma cells was sustained for 14 days for most other vaccines. Typically, PSV23 requires frequent re-immunization every 5 years due to a rapid decline of antibody titers. The swift deterioration of ASC in our in vitro cultures could reflect the lack of LLPC maintenance after this particular vaccine. In contrast, ASC after tetanus, MMR (a live attenuated vaccine), and trivalent influenza vaccination showed higher ASC frequencies on day 7-8 and maintained to day 14. Interestingly, tetanus and MMR are vaccines with greater durability requiring boosters every 10 to 20 years due to prolonged half-lives. Hence, the durability of ASC survival at 2 weeks using our in vitro BM culture system provides possible effective novel assays to define vaccine biomarkers of longevity.

The specific survival factors secreted by the BM MSC are not well characterized. Proteins, lipids, or even carbohydrates are all possible candidates. The role of IL-6 is important since inhibition show decreases in ASC survival in culture. However, the IL-6 receptor expression was reduced on human LLPC compared to other BM plasma cell subsets. Extracellular matrix proteins such as heparin sulfate, collagen, laminin, and fibronectin may prove to be important along with additional cytokines such as IL-10, IL-5, and APRIL.

Experimental Methods

The cells in the human BM microniche indeed provide factors to maintain peripheral blood ASC survival and function. Using IgG ELISpot assays that can measure single plasma cell survival and function, co-cultures of BM supporting cells and exogenous cytokines were evaluated in hypoxic conditions to examine the ex vivo survival of human primary circulating ASC for several months.

Peripheral blood ASC died quickly ex vivo but survived and functioned for weeks in co-cultures with human BM derived MSC. Circulating ASC (identified by CD19+ CD38hiCD27hi) were FAC sorted 7 days after vaccination and cultured multiple replicates with conventional media (RPMI with 8% fetal bovine serum (FBS) or with human BM-derived MSC cultures for 4-7 days).

FAC sorted ASC were cultured per well. On day 0, ELISpots were performed to enumerate the total IgG secreting cells per well. Then, each specified day, ASC in media alone or ASC in MSC co-cultures were harvested and IgG ELISpot assays were performed. Percentages of IgG ASC ELISpots from day 0 were calculated. In media alone, very few ASC were detected on day 1 and none by day 3 (FIG. 1A). In contrast, ASC in co-cultures survived for 6 days (on day 1, 2, 3, 4) until they were intentionally terminated. Furthermore, ASC remained functional and continued to secrete Ig until day 6 of the co-cultures. Culture media of the co-cultures from day 0 to day 6 showed increasing Ig secretion which accumulated in the co-cultures.

On day 1 of the co-cultures, ASC ELISpot frequencies often increased greater than 300-500% compared to spot numbers on day 0 from multiple samples. To examine whether staining and/or sorting affected yields of circulating ASC, ELISpots were measured from the equal numbers of peripheral blood mononuclear cells (PBMC) with and without staining and/or FAC sorting compared to untouched PBMC. To assess the role of high pressure sorting, total PBMC were recovered after the process of high pressure FACS and found the same number of PBMC had only 37±4% of the spot numbers of unsorted PBMC. If we stained and sorted the total PBMC, they had even lower recovery 26±2% of the controls (FIG. 1B). Surface staining did not decrease overall spot numbers, however, total Ig secretion per cell was reduced as evident by the increased background. This result suggested that ASC function of Ig secretion is affected by FAC sorting.

The majority of circulating terminally differentiated ASC after vaccination are Ki67+ suggesting active proliferation or recent proliferation. Whether the increased frequencies of ASC after sorting on day 1 were due to active proliferation or revival of "non-functional" ASC that had recently proliferated was evaluated with BrdU incorporation in the ASC co-cultures from two separate donors (FIG. 1C). Cultures with non-irradiated MSC or (proliferating MSC) were used as positive controls. On both days 2 and 3, irradiated MSC (iMSC) alone or together with blood ASC co-cultures had no incorporated BrdU. This was in direct comparison to controls of proliferating non-irradiated MSC. Hence, blood ASC do not proliferate but "recover" from a "stunned" non-secretory state after FACS isolation when placed on iBM-MSC co-cultures.

Co-cultures beyond 7 days were often difficult to maintain due to MSC proliferation. To limit MSC proliferation, MSC (iMSC) were irradiated in the co-cultures and demonstrated pro-survival support to the blood ASC similar to non-irradiated MSC for 7 days. Ratios of ASC-iMSC co-cultures of 1:2, 1:3, 1:5, 1:8, 1:10, 1:12, 1:15, and 1:20 were performed, and it was found that 1:10 was the optimal ratio for ASC survival.

The duration of the ASC pro-survival support was extended with iMSC and so we co-cultured iMSC and ASC for months. Sorted ASC 7 days after vaccination from the blood were cultured in replicates from two separate subjects and harvested on subsequent days from day 0, 1, 2, 3 and weekly up to day 30 or 45. Sorted ASC were cultured per well in multiple replicates from each of the 2 subjects and IgG ELISpots were performed on the specified days when the cells were harvested. Approximately 50% of the original IgG ASC (from day 0) were able to secrete IgG from weeks 1 to 2. It was found that 32 and 38% of total IgG plasma cells could survive and function for up to 31 days when the cultures were intentionally terminated (FIG. 1D). Eventually the IgG secretion in the co-cultures did wane after one month suggesting replenishment of iMSC or additional factors are needed to sustain long-lived human plasma cell survival.

To understand if ASC survival and function required cell-cell contact, ASC were cultured in iMSC per well in transwells (4 μm pore size), co-cultures, or media alone. Both IgG ELISpot frequencies in iMSC:ASC co-cultures and transwells were similar showing that cell-cell contact was not necessary for ASC survival. Again, ASC in media alone died within one day. To test if secreted MSC factors provided ASC survival, soluble secreted factors were isolated from MSC cultures and found that the MSC secretome alone provided ASC survival equal to co-cultures and transwells for 7 days (180% of day 0) (FIG. 2). For long-term cultures, the MSC secretome supported ASC survival and IgG secretion for up to 65 days. Longer cultures may have sustained ASC survival for months demonstrating the importance of the MSC secretome in the human BM microniche.

TNF-ligand superfamily cytokines (APRIL and BAFF) have an important role in the survival of B and plasma cells; however, APRIL is featured prominently for plasma cells. B cell maturation antigen (BMCA), a TNF receptor superfamily (TNFRS17) receptor for APRIL is highly expressed on all human BM plasma cells including the LLPC. APRIL and BAFF were tested with the MSC secretome of ASC isolated from the blood 7 days after immunization. Exogenous APRIL or BAFF alone had no effect on the survival of ASC (FIG. 3).

Although APRIL alone did not provide a survival advantage, APRIL was tested together with the MSC secretome and found enhanced ASC survival by 50-300% on day 1 to 7 (FIG. 3). The addition of BAFF into the MSC secretome cultures resulted in no pro-survival effect. This phenomenon was consistently observed among six different subjects with multiple vaccines that included: the 23-valent pneumococcal carbohydrate vaccine (PSV23), tetanus, MMR, and influenza vaccines for up 14 days. By day 7-8 of the ASC cultures with APRIL and MSC secretome, most ASC from these vaccinated subjects remained higher than 150% of day 0.

To test the importance of hypoxia, circulating ASC were isolated from a healthy adult and compared BM secretome cultures of ASC under normoxia or hypoxia (2.5% O2) with and without exogenous APRIL. IgG ASC survival in hypoxia (96±3%) was better compared to normoxic conditions (52±3%) on day 13 in the BM secretome without APRIL (FIG. 4A). With the addition of APRIL, the ASC frequencies between the hypoxic and normoxic conditions were similar up to day 7. However, the ASC survival was superior in hypoxia after 2 weeks in culture with frequencies of 222%±31 compared to normoxia 184%±22. This difference was sustained on days 20, and 27 with IgG frequencies of 182%±6 and 135%±9 in hypoxia and 131%±16, 93%±13 in normoxia respectively. These differences demonstrate the importance of hypoxia in maintaining survival of circulating ASC in culture.

To test whether ASC after vaccination could also be sustained for months in culture, peripheral blood ASC was isolated 7 days after tetanus immunization. Without APRIL, ASC survived in BM secretome (34%±3) on day 14 in similar fashion as the iMSC co-cultures in FIG. 1 under normoxic conditions. In hypoxia, a slightly higher number of ASC survived (58%±5) compared to those in normoxia on day 14 to 56 but did not reach statistical significance. However, the MSC secretome with APRIL in hypoxic conditions demonstrate a significant enhancement of ASC survival in the BM secretome from days 14, 21, 28, 35, 42, 49, and 56 (208%±7, 188±9, 181±9, 177±8, 166±16, 147±8 125±9) compared to normoxic conditions (173%±6, 140±9, 134±6, 124±8, 104±10, 80±11, 58±10). The paracrine effects of the BM MSC secretome together with APRIL in hypoxic conditions enhance survival of blood ASC (125% of day 0) in vitro for over 50 days.

BM-Derived Mesenchymal Stromal Cells (BM-MSCs)

The source for the BM-MSCs used was chiefly bone marrow aspirate (BMA) of healthy donors. Briefly, BM mononuclear cells (MNCs) were isolated by Ficoll-Hypaque (GE Healthcare) or Lymphocyte Separation Medium (LSM; Cellgro/Corning) density-gradient centrifugation. Adherent cells were classified as primary BM-MSCs and further propagated ex vivo for subsequent uses, which were generally between their 3rd and 8th passages. Irradiated BM-MSCs were exposed to γ-irradiation at ~76.6 (~0.766 Gy) rad per minute for 40 minutes (so totaled ~30.64 Gy).

BM MSC Secretome

Supernatants were harvested daily for one week from BM MSC cultures monolayer cultures. Pooled supernatants were centrifuged to remove floating cell debris. Fresh or thawed SBMC aliquots were either used within two weeks or discarded.

Isolation of Peripheral Blood Mononuclear Cells (PBMCs) and ASC

PBMCs were separated from freshly collected PBL samples by Ficoll-Hypaque (GE Healthcare) or Lymphocyte Separation Medium (LSM; Cellgro/Corning) density-gradient centrifugation. T cells and monocytes were removed by CD3 and CD14 beads (Miltenyi) and flow through stained with the following panel (anti-CD19: BD Bioscienc, CD3: CD14, CD27, IgD, CD38, and CD138) The PB populations were generally ~85-99% pure, as assessed by flow cytometric re-analysis of post-sort cells.

Establishment of In Vitro Culture Systems for Human Blood ASCs.

BM-MSCs as feeder (co-cultures on adherent monolayer) were co-cultured in 96-well flat-bottom cell culture plates or transwells (0.4 μm pore polycarbonate insert membrane of 96-well plates (Corning/Sigma)) in 37° C. in a humid, 5% CO2, 95% air (20% $O_2$) incubator or in hypoxic culture conditions (2.5% 02) at 37° C. in a modular incubator chamber (Billups-Rothenberg) that was infused with a pre-analyzed gas mixture containing 2.5% $O_2$, 5% $CO_2$, and 92.5% $N_2$ (AirGas). The initial input seeding CD27hiCD38hi ASC numbers for each culture varied (~233 to ~3,982 cells) dependent upon the total post-sort cells. The same per-well numbers of ASC were also reserved for immediate use right after sorting (day 0 post-sort). In MSC secretome media, ASC alone were cultured with factors (stimuli or inhibitors) for specified days. For MSC-free cultures, MSC secretome or RPMI with 10% fetal bovine serum (R10) were included as (negative) "controls". Cells were harvested on designated days and enzyme-linked immunospot (ELISpot) IgG assays were performed and the supernatants were used for IgG ELISAs. Cultured ASCs and supernatants were generally assayed at different time points—typically at days 1, 3, 7, and for all the weeks that followed—until all cultured wells were purposely used up (up to 2-3 months). The blood ASC survival and function/IgG secretion were assessed by ELISpot assays, and their output values were expressed as the percentage of viable/surviving ASCs as compared to those detected at the start of the culture (at day 0).

Exogenous factors included a variety of cytokines and growth factors, IL-5, IL-6, APRIL, BAFF, Osteopontin, IFNg, TNFalpha (R&D), IL-21 (Peprotech), and CXCL12 (Rockland) added to cultures at day 0 of blood ASCs. The final concentrations of the added factors, which were optimized based on titrated experiments and the manufacturer's recommendations.

BrdU Cell Proliferation Assays

Blood ASC cellular proliferation was evaluated on the basis of bromodeoxyuridine (BrdU) incorporation and using the BrdU Cell Proliferation Assay kit (Millipore), according to the manufacturer's instructions. Briefly, BrdU (1:100 finally diluted, in MSC-med or SBMC from Millipore's BrdU solution; 100 μL/well) was administered at the beginning (day 0) of blood ASC cultures, which were set up both on iBM-MSCs and in SBMC (5,000 ASCs/well; 1:10 ASC:MSC cell ratios). Controls included BM-MSCs (as proliferative cell control), and irradiated BM-MSCs (as non-dividing cell control). Cells were then incubated at 37° C. in the air incubator (5% CO2). At 48- and 72-hrs time points, cells were gently washed twice with PBS by centrifuging at 500×g for 10 minutes at RT. The assay was performed in duplicate and for two unrelated blood ASC samples.

---

The invention claimed is:

1. A cell culture composition comprising antibody producing cells, exogenously added IL-6, fibronectin, and a saccharide, and wherein the exogenously added IL-6 and fibronectin are proteins in secretions of mesenchymal stromal/stem cells (MSCs).

2. The cell culture composition of claim 1, wherein proteins in secretions of mesenchymal stromal/stem cells (MSCs) are derived from extracting the proteins from a group of mesenchymal stromal/stem cells (MSCs).

3. The cell culture composition of claim 1, wherein proteins in secretions of mesenchymal stromal/stem cells (MSCs) are derived from replicating mesenchymal stromal/stem cells (MSCs) in the growth medium.

4. The cell culture composition of claim 1, wherein proteins in secretions of mesenchymal stromal/stem cells (MSCs) are derived from non-replicating mesenchymal stromal/stem cells (MSCs) in the growth medium.

5. The cell culture composition of claim 1 in an enclosure wherein the amount of oxygen is less than 5% by volume.

6. The cell culture composition of claim 1, wherein the growth medium further comprises exogenously added APRIL.

7. The cell culture composition of claim 1 further comprising an exogenously added buffering agent, amino acids, and vitamins.

\* \* \* \* \*